United States Patent [19]

Whitehead et al.

[11] 4,194,115
[45] Mar. 18, 1980

[54] METHOD AND MEANS FOR HELIUM/HYDROGEN RATIO MEASUREMENT BY ALPHA SCATTERING

[76] Inventors: Robert A. Frosch, Administrator of the National Aeronautics and Space Administration, with respect to an invention of A. Bruce Whitehead, Wayzata, Minn.; Thomas A. Tombrello, Altadena, Calif.

[21] Appl. No.: 958,573

[22] Filed: Nov. 7, 1978

[51] Int. Cl.² ............................................. G01N 23/00
[52] U.S. Cl. .................................... 250/308; 250/307
[58] Field of Search ............... 250/308, 364, 393, 394, 250/395, 370

[56] References Cited

U.S. PATENT DOCUMENTS

| | | | |
|---|---|---|---|
| 2,740,894 | 4/1956 | Deisler et al. | 250/308 |
| 3,102,199 | 8/1963 | Zito | 250/308 |
| 3,171,962 | 3/1965 | Ballinger | 250/308 |

*Primary Examiner*—Bruce C. Anderson
*Attorney, Agent, or Firm*—Monte F. Mott; John R. Manning; Paul F. McCaul

[57] ABSTRACT

Apparatus and method for determining helium to hydrogen ratios in a gaseous sample by measurement of forward scattering products due to alpha particle collisions with helium and hydrogen contained within the gaseous sample. More specifically, an apparatus is disclosed in which a gaseous sample, contained within an enclosure, is bombarded by alpha particles created by a self contained radioactive source. Baffles are positioned in the enclosure so that only scattering products falling within a predetermined forward scattering angular range can impact a detector assembly. In an embodiment scattered particles are detected by two detectors mounted in tandem, the first completely blocking the second detector with respect to incident scattering products. This embodiment is based on the principle that scattering products have a forward scattering angle $\theta$ greater than 15 degrees due to alpha particle/hydrogen collisions comprise only recoil protons. For a given kinetic energy, recoil protons will penetrate farther into silicon detector material than will scattering products from alpha particle/helium collisions. Thus, an apparatus according to the teachings of the invention identifies alpha particle/hydrogen or alpha particle/helium collisions primarily by whether scattering product impacts occur simultaneously in both the first and second detectors or occur only in the first detector. Relative magnitudes of the two pulses can be used to further discriminate against other effects such as noise and cosmic ray events.

10 Claims, 6 Drawing Figures

METHOD AND MEANS FOR HELIUM/HYDROGEN RATIO MEASUREMENT BY ALPHA SCATTERING

ORIGIN OF INVENTION

The invention described herein was made in the performance of work under a NASA contract and is subject to the provisions of Section 305 of the National Aeronautics and Space Act of 1958, Public Law 85-568 (72 Stat. 435; 42 USC 2457).

FIELD OF THE INVENTION

This invention relates to apparatus and methods for determining the ratio of helium to hydrogen in a sample gas by measurement of energy loss of scattering products within a predetermined forward scattering angle caused by collisions of alpha particles with hydrogen and helium contained within the sample gas.

BACKGROUND OF THE INVENTION

Hydrogen and helium constitute ninety-nine percent of the matter in the solar system. The helium-to-hydrogen ratio of the material from which the solar system was formed is an essential ingredient in all stellar evolution calculations. It reflects the conditions of the first few minutes of the "big bang" and forms a boundary condition for modeling the evolution of our own star. One way to determine this ratio is to study the sun because it contains most of the mass of the solar system. However all measurements are quite indirect and subject to uncertainties in interpretation. The giant planets, particularly Jupiter, should be composed of original solar nebula material and are considered to be good indicators of the initial solar system composition. Thus measurement of helium to hydrogen ratios is an extremely important objective of any mission to the outer planets.

A number of techniques have been considered for making helium to hydrogen ratio measurements. These techniques include mass spectrometry, gas chromatography and differential pressure measurements. Alpha scattering was used to measure chemical composition of lunar material by unmanned lunar landing spacecraft. However these alpha scattering measurements were based on back scattering of alpha particles in which the lunar soil formed a thick target. Observation of scattered alpha particles at backward angles allowed maximum separation of detected materials. This previously utilized technique is unsuitable for helium and hydrogen measurements because their scattering products occur in a forward hemisphere.

SUMMARY OF THE INVENTION

The present invention eliminates the problems described above by providing an apparatus and method for measuring the ratio of helium to hydrogen in a gaseous sample by measurement of scattering products within a predetermined forward scattering angular range due to alpha particle/hydrogen collisions and alpha particle/helium collisions. The invention discloses a new geometry and mode of operation for an alpha-scattering chemical analysis instrument suitable, among other purposes, for use by an outer planet probe to measure helium to hydrogen ratios in planetary atmospheres. The apparatus comprises a source for directing alpha particles into a gaseous sample, a means for isolating scattering products within a predetermined forward scattering angular range resulting from collisions between the alpha particles and the gaseous sample, a means for detecting the isolated scattering products, a means for identifying the detected isolated scattering products which result from alpha particle/hydrogen collisions, and a means for identifying the detected isolated scattering products due to alpha particle/helium collisions. The invention also discloses an apparatus whereby predetermined forward scattering angular ranges can be defined by appropriate positioning of blocking baffles within an enclosure containing the sample gas, the alpha particle source, and a detector assembly capable of providing an output proportional to scattering products contained within various predetermined forward scattering angles.

An embodiment according to the teachings of the invention provides a two-detector assembly, the two detectors being mounted in tandem. Scattering products having identical kinetic energies from alpha particle/hydrogen collisions, which comprise only hydrogen nuclei at forward scattering angles greater than 20 degrees, will penetrate deeper into a detector material than scattering products from alpha particle/helium collisions which comprise alpha particles. Thus, an apparatus is disclosed which provides a means for determining whether a scattering product within a predetermined forward scattering angle is totally absorbed within the first detector or is only partially absorbed within the first detector and partially absorbed within the second detector. If for a single impact event an output is provided by both the first and second detectors then that event resulted from an alpha particle/hydrogen collision. If on the other hand, an output is provided only by the first detector, then that event resulted from an alpha particle/helium collision. By counting both types of events and referring to an experimentally determined set of calibration curves, the ratio of helium to hydrogen within the gaseous sample is determined.

DETAILED DESCRIPTION

As required, a detailed illustrative embodiment of the invention is disclosed herein. This embodiment exemplifies the invention and is currently considered to be the best embodiment for such purposes. However, it is to be recognized that other blocking and detection techniques could be utilized in order to isolate scattering products occuring within predetermined forward scattering angular ranges. Accordingly, the specific embodiment disclosed is representative in providing a basis for the claims which define the scope of the present invention.

As previously explained, the present invention discloses an apparatus and method for measuring the ratio of helium to hydrogen in a gaseous sample. This ratio is determined by directing a source of alpha particles into a gaseous sample, isolating scattering products from collisions between the alpha particles and hydrogen and helium present in the gaseous sample from those which occur within a predetermined scattering angular range, detecting the thus isolated scattering products, and identifying the detected scattering products as being created either by alpha particle/hydrogen collisions or alpha particle/helium collisions. In accordance with a specific embodiment the identification is accomplished by determining the origin of each scattering product by whether it passes through a first detector and is absorbed by a second detector, or whatever it is completely absorbed by the first detector. The two detectors are mounted in tandem, the first detector being of sufficient thickness to stop scattering products resulting from alpha particle/helium collisions, but of insufficient thickness to stop scattering products resulting from alpha particle/hydrogen collisions. By processing the outputs of both detectors in conjunction with a coincidence detecting device, an output from the first detector not having a corresponding output from the second detector is identified as resulting from an alpha particle/helium collision, whereas a simultaneous output from both the first and second detectors is identified as resulting from an alpha particle/hydrogen collision. By counting the pulses formed in the above-described manner, and by utilizing calibration curves determined under known conditions, the ratio of helium to hydrogen within the gaseous sample can be determined.

Figure 1:
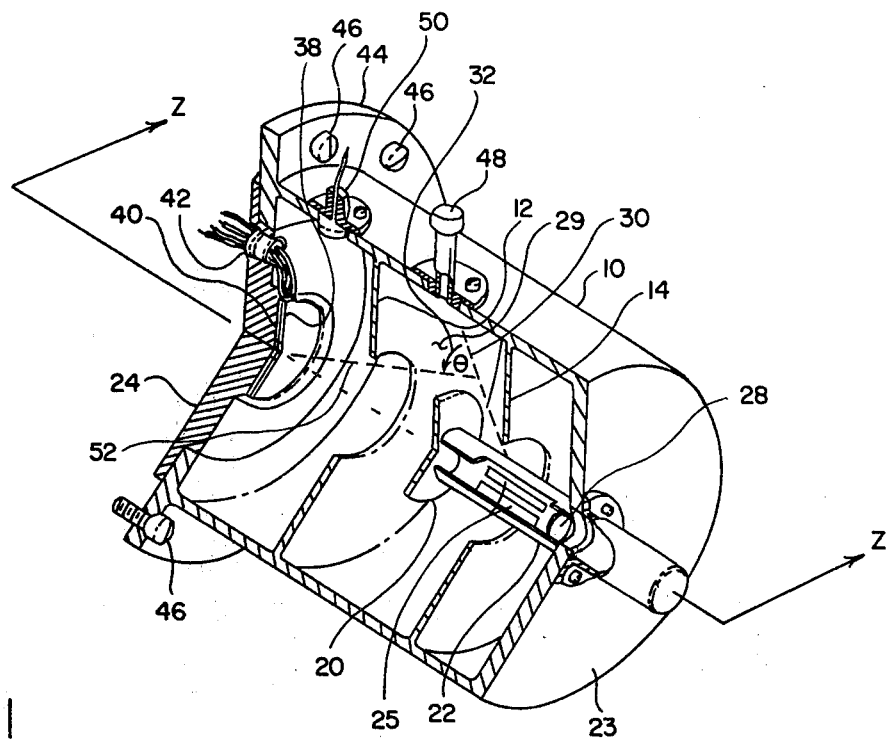
FIG. 1 is a perspective, partially cut away view of an apparatus according to the present inention.
Figure 2:
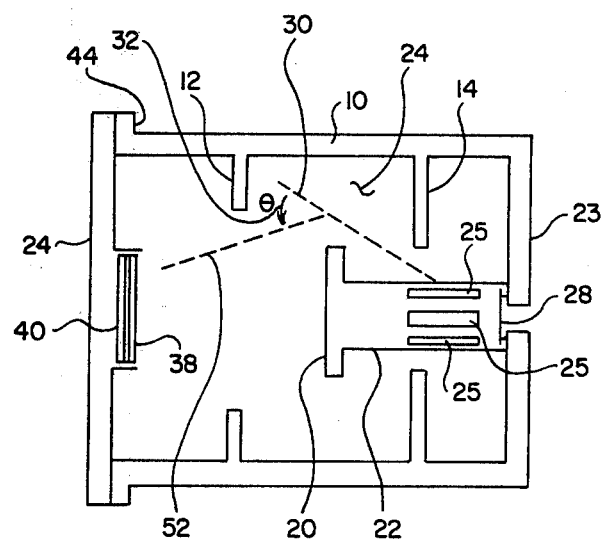
FIG. 2 is a simplified cross-sectional view taken along line 2—2 of FIG.

Referring now to FIGS. 1 and 2, an apparatus according to the present invention comprises a cylindrically shaped enclosure 10 having first and second angularly shaped baffles 12 and 14 respectively, the baffles extending inwardly into the enclosure 10. A centrally dispersed baffle or blocking shield 20 is supported by a hollow cylindrical support post 22 centrally attached to one end 23 of the enclosure 10, the other end being sealed by a removable end plate 24. A plurality of longitudinally extending slots 25 are disposed around the circumference of the support post 22 to allow alpha particles from an alpha particle source 28 to be ejected into a scattering region 29 of the enclosure as shown by the dotted line at 30. Although only two baffles 12 and 14 are shown, other baffle configurations could be utilized depending on the desired range of forward scattering angles θ as shown at 32. It has been found that deletion of the first and second baffles 12 and 14 does not significantly increase the background counting rate. It is theorized that this is because there is a low probability of particle scattering from the enclosure 10 walls at relative low angles of incidence.

First and second silicon detectors 38 and 40 respectively are centrally disposed on the inner surface of the removable end plate 24. An access plug 42 is provided in the removable end plate 24, the plug 42 providing access to voltages developed in the first and second detectors 38 and 40. The cylindrically shaped enclosure 10 is formed so that the end interfacing with the removable end plate 24 is in the shape of a flange 44, the flange 44 having mounting bolts 46 for convenience in attaching the enclosure 10 to a suitable holding structure. A sample gas containing helium and hydrogen is inserted into the enclosure 10 via a gas input valve 48. A pressure-monitoring transducer 50 is also provided, pressure being one parameter utilized to predict energy loss of ejected alpha particles. The first and second detectors 38 and 40 respectively are mounted in tandem so that a forward scattering product as represented by the dotted line at 52 must pass through the first detector 38 in order to reach the second detector 40. This detector configuration provides a means for distinguishing between alpha particle/helium collisions and alpha particle/hydrogen collisions in the sample gas by determining whether the scattering product due to each alpha particle collision is stopped by the first detector 38, or passes through the first detector 38 and is stopped by the second detector 40.

Figure 3:
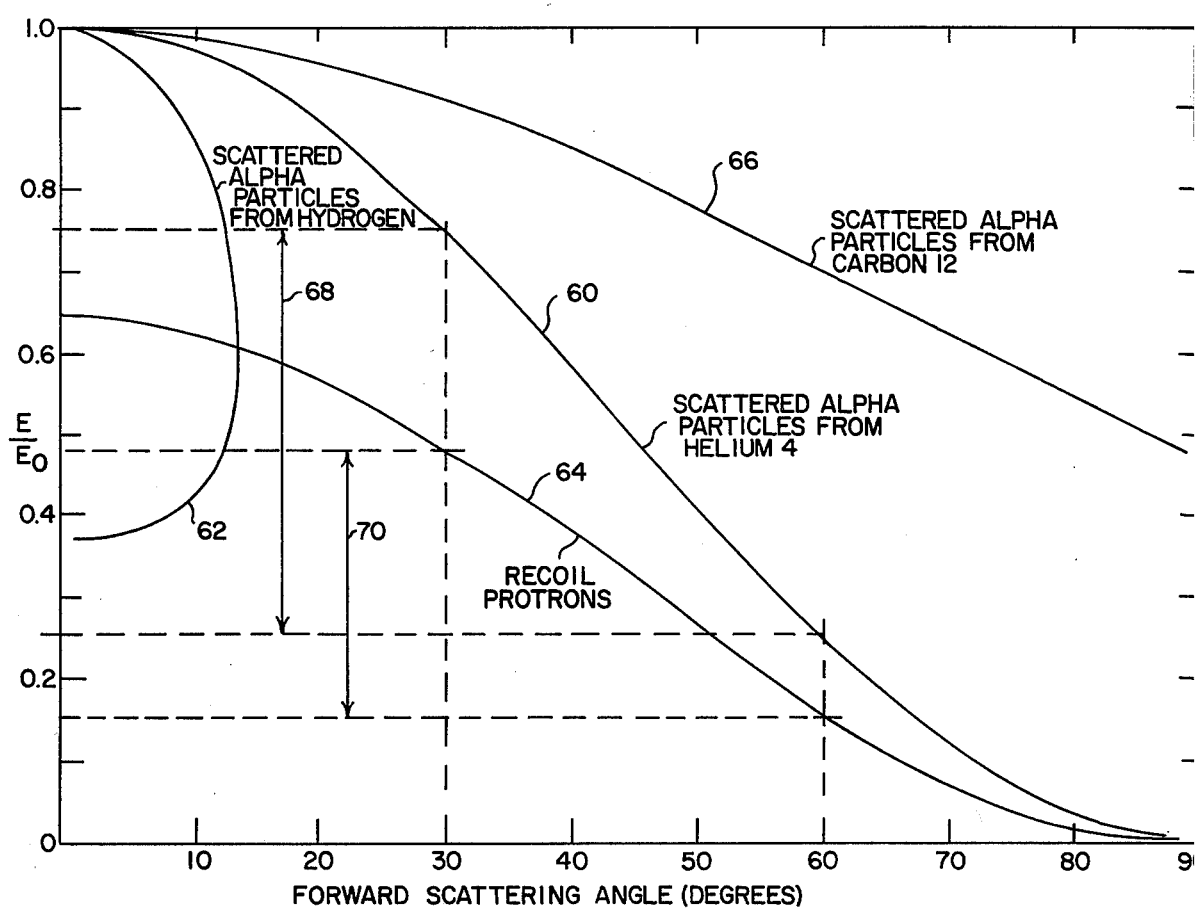
FIG. 3 is a graph showing kinetic energy of scattering products within a forward scattering angle between 30 and 60 degrees due to alpha particle/hydrogen collisions and alpha particle/helium collisions.

In order to understand operation of the apparatus shown in FIGS. 1 and 2, it is necessary to understand the characteristics of forward scattering products resulting from alpha particle/hydrogen collisions and alpha particle/helium collisions. Referring to FIG. 3, the relationship between the energy of scattered products with respect to the energy of a bombarding alpha particle as a function of forward scattering angle can be seen. $E_O$ is the kinetic energy of the alpha particle before scattering. A helium curve 60 shows this relationship in helium 4 as a function of the forward scattering angle. At a forward scattering angle of 30 degrees, for example, approximately 75 percent of the energy contained within the bombarding alpha particle is imparted to a scattered alpha particle. Hydrogen, on the other hand, exhibits a different energy characteristics depending on whether an alpha particle is scattered or whether a recoil proton is scattered, the proton comprising a nucleus of a hydrogen atom. As can be seen, alpha particle/hydrogen collisions only result in scattered alpha particles occurring within forward scattering angles less than approximately 15 degrees as shown by curve 62. On the other hand recoil protons shown in curve 64 have energy throughout the forward hemisphere; for example, at a forward scattering angle of 30 degrees approximately 48 percent of the energy of a colliding alpha particle is imparted to a recoil proton. FIG. 3 also shows the energy of scattered alpha particles from carbon 12 as shown in curve 66.

The apparatus provides a means to discriminate between alpha particles and helium nuclei scattered by alpha particle/helium collisions and protons scattered by alpha particle/hydrogen collisions even though the energy ranges of the various scattering products overlap. Again referring to FIG. 3, it can be seen that forward scattering angles between approximately 20 and 60 degrees provide significant energy separation between scattering products from alpha particle/hydrogen and alpha particle/helium collisions. Angles less than 20 degrees provide inadequate separation between helium scattered products and heavier nuclei such as carbon 12. Above 60 degrees, the energy of the scattered particles is too low. Elastic scattering cross-sections, well known in the art, show that there is a resonance in helium scattering which results in a minimum at approximately 30 degrees. Elastic scattering cross-sections also show that in the angular region between 30 and 60 degrees an incident alpha particle should have an energy in excess of 6 MeV, the cross-section almost vanishing at 5 MeV. As a result of the above, the alpha particle source 28 should provide alpha particles having an energy in excess of 6 MeV to create scattering products between forward angles of 30 and 60 degrees. As can be seen from FIG. 3, for forward scattering angles between 30 and 60 degrees scattering products from alpha particle/helium collisions will have energy levels between approximately 25% and 75% of the original alpha particle energy as shown at 68. Similarly, recoil protons resulting from alpha particle/hydrogen collisions will have energies between 15 and 48 percent of the original alpha particle energy as shown at 70.

Figure 4:
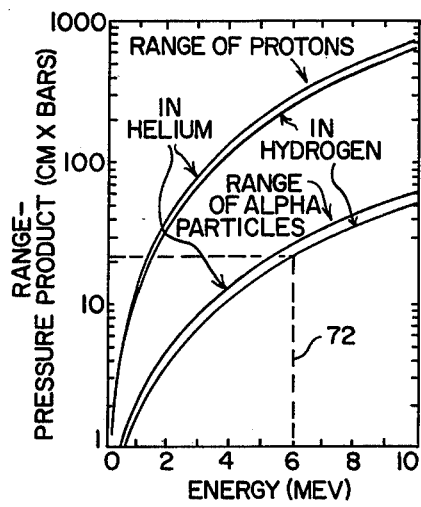
FIG. 4 is a graph showing the range-pressure product of alpha particles and protons in helium and hydrogen as a function of kinetic energy.

Sizing of the cylindrically shaped enclosure 10 is influenced by the energy loss of alpha particles as they pass through the gaseous sample. The range of an alpha particle in a sample gas is a function of the original energy of the alpha particle and the pressure of the sample gas. These relationships are shown in FIG. 4 which shows that an alpha particle having an energy level of 6 MeV will have a range-pressure product of approximately 22 cm. bars as shown at 72. If it is desired that the ratio measuring apparatus operate with sample gas pressures between 0.1 and 1 bar, it then is theorized that a longitudinal dimension of 6.1 cm. for the cylindrical enclosure 10 and a 5 cm. inner diameter will be adequate for proper operation.

Figure 5:
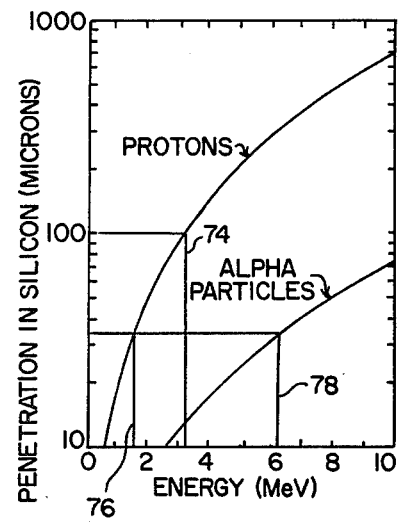
FIG. 5 is a graph showing the penetration depth of protons and alpha particles in silicon as a function of energy.

The first and second detectors 38 and 40 respectively have been chosen to be gold silicon surface barrier detectors mounted in tandem as previously explained. Referring to FIG. 5, the penetration depth in silicon of various scattering products as a function of their energy levels can be seen. For example, a proton having kinetic energy of slightly over 3 MeV's will travel approximately 100 microns in silicon as shown at 74, whereas the same proton having a kinetic energy of approximately 1.5 MeV's will travel 35 microns as shown at 76. Similarly, an alpha particle having an energy level less than 6 MeVs will travel less than 35 microns in silicon as shown at 78. Based upon the data shown in FIG. 5, the first detector 38 was chosen to have a thickness of approximately 35 microns, and the second detector chosen to have a thickness of at least 100 microns. Thus, the first detector 38 is sufficiently thick to stop any proton having a kinetic energy less than 1.5 MeV's and any alpha particle having a kinetic energy less than 6 MeV's. Protons having a kinetic energy between 1.5 and 3.0 MeV's will traverse the first detector 38 and be stopped by the second detector 40, thereby providing a signal in both. The sum of the energy absorbed by each of the detectors 38 and 40 represents the energy of the impacting proton. Thus, each particle impacting the first detector 38 and having an energy greater than 1.5 MeV's can be distinguished according to whether a single output pulse is provided by the first detector 38 or whether both detectors 38 and 40 provide substantially simultaneous output pulses. Since the detector combination can not distinguish protons from alpha particles if their energy levels are below 1.5 MeV's, that portion of the energy spectrum is not utilized. It is theorized that the alpha particle source 28 could be Polonium 214 which emits alpha particles having an energy of 7.7 MeV's in the Radium-226 decay chain. However, other radioactive sources could be utilized such as Polonium 212 which emits an 8.5 MeV alpha particle and occurs in the Thorium decay chain.

Figure 6:
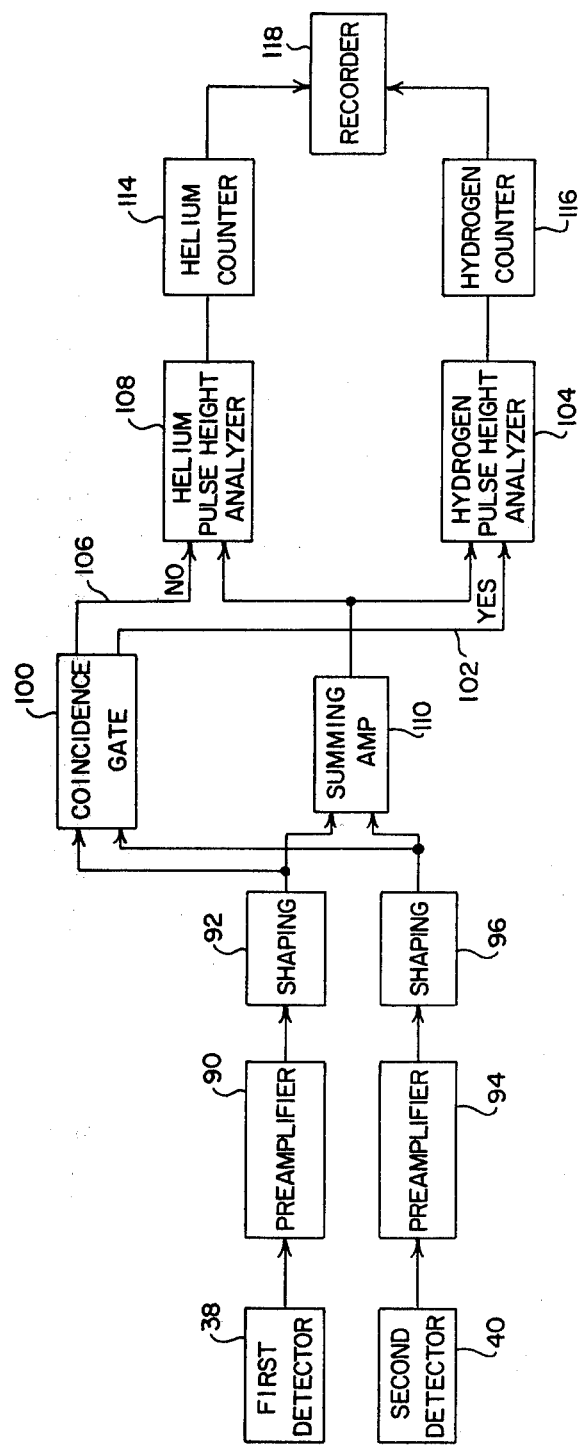
FIG. 6 is block diagram of an electronic processing system according to the invention.

Processing of output pulses provided by the two detectors 38 and 40 can be understood by referring to the block diagram shown in FIG. 6. Outputs from the first detector 38 are amplified by a preamplifier 90 and shaped by a shaping network 92. Similarly, outputs from the second detector 40 are amplified by a second pre-amplifier 94 and shaped by a shaping network 96.

Outputs from the first detector shaping network 92 and the second detector shaping network 96 are provided to a coincidence gate 100. If both detectors 38 and 40 have simultaneous output pulses, the coincidence gate 100 provides an enabling pulse on line 102 in turn enables a hydrogen pulse height analyzer 104. If only the first detector 38 has an output pulse, the coincidence gate 100 provides an enabling pulse on line 106 which in turn enables a helium pulse height analyzer 108. Outputs from the first detector shaping network 92 and the second detector shaping network 96 are provided to a summing amplifier 110, the output of which is provided to both the helium pulse height analyzer 108 and hydrogen pulse height analyzer 104. Thus, if an input from the first detector shaping network 92 only is received by the coincidence gate 100, an enabling pulse is provided on line 106 and opens a gate within the helium pulse height analyzer 108, thereby allowing an output from the summing amplifier 110 to be measured and counted by a helium counter 114. In a similar manner if the coincidence gate 100 receives simultaneous outputs from both the first and second detector shaping networks 92 and 96, an enabling pulse is provided on line 102 and opens a gate within the hydrogen pulse height analyzer 104, thereby allowing an output from the summing amplifier 110 to be measured and counted by a hydrogen counter 116. A recorder 118, which could be a conventional magnetic tape recorder, then records the number of counts and energy level of each signal provided by the helium counter 114 and the hydrogen counter 116, the ratio of the number of helium counts to the number of hydrogen counts being proportional to the helium/hydrogen ratio in the sample gas.

As an alternative, a pulse height analysis can be accomplished by discriminators and scalers can accumulate the number of events of the two types (scattering from helium and recoil from hydrogen) during a common time interval.

What is claimed is:

1. An apparatus for providing data useful in a determination of the ratio of helium to hydrogen in a gaseous sample; comprising:

a source for directing alpha particles into said gaseous sample;

isolation means for isolating scattering products contained within a predetermined forward scattering angular range, said scattering products resulting from collisions between said alpha particles and said gaseous simple;

detection means for detecting said isolated scattering products;

first identification means for identifying said detected isolated scattering products resulting from alpha particle/hydrogen collisions; and second identification means for identifying said detected isolated scattering products resulting from alpha particle/helium collisions whereby the ratio of helium to hydrogen is determinable from the ratio of the products of said second and first identification means, respectively.

2. The apparatus of claim 1 in which said isolation means comprises:

an elongated enclosure containing said gaseous sample and having said alpha particle source located at one end and said detection means at the other end;

a plurality of baffles extending inwardly from said enclosure inner walls; and a blocking shield spaced-apart from said detection means and positioned to block a straight-line path from said alpha particle source to said detection means, said blocking shield and said baffles being located so that only scattering products within said predetermined forward scattering angular range can be detected by said detection means.

3. The apparatus of claim 2 in which said predetermined forward scattering angular range is between approximately 30 and 60 degrees, further comprising:

said detection means comprising a first surface barrier detector and a second surface barrier detector, said first and second detectors being mounted in tandem and positioned so that said first detector faces into said enclosure, said first detector being chosen to have a thickness sufficiently great to absorb substantially all of the energy of scattering products due to alpha particle/helium collisions and to pass a portion of the energy of scattering products due to alpha particle/hydrogen collisions, said second detector being chosen to have a thickness sufficiently great to absorb the energy of alpha particle/hydrogen scattering products not absorbed by said first detector;

said first identification means for identifying scattering products resulting from alpha particle/hydrogen collisions comprises means to identify substantially simultaneous output pulses from said first and second detectors; and said second identification means for identifying scattering products resulting from alpha particle/helium collisions comprises means to identify output pulses from said first detector only.

4. The apparatus of claim 3 in which said alpha particle source is Polonium 214, said first detector is a totally depleted gold-silicon surface barrier detector approximately 35 microns thick, and said second detector is a gold-silicon surface barrier detector approximately 100 microns thick.

5. The apparatus of claim 2 further comprising means to measure the pressure of said gaseous sample within said enclosure.

6. An apparatus for providing data useful in a determination of the ratio of helium to hydrogen in a gaseous sample, comprising:

a source for directing alpha particles into said gaseous sample whereby said alpha particles will collide with said helium and hydrogen;

means for isolating scattering products due to collisions between said alpha particles and said gaseous sample to scattering products which occur within a predetermined forward scattering angular range;

means for detecting said isolated scattering products comprising a first surface barrier detector and a second surface barrier detector, said first and second detectors being mounted in tandem and positioned so that said first detector is impacted first by said isolated scattering products, said first detector being chosen to have a thickness sufficiently great to absorb substantially all of the energy of isolated scattering products due to alpha particle/helium collisions and to pass a portion of the energy of isolated scattering products due to alpha particle/hydrogen collisions, said second detector being chosen to have a thickness sufficiently great to absorb the energy of isolated scattering products due to alpha particle/hydrogen collisions not absorbed by said first detector;

first means for counting each isolated scattering product having a kinetic energy within a predetermined range that impacts said first detector but not said second detector thereby identifying an alpha particle/helium collision; and second means for counting each scattering product having a kinetic energy sufficiently great to pass through said first detector and being at least partially absorbed by said second detector thereby dentifying an alpha particle/hydrogen collision whereby the ratio of helium to hydrogen is determinable from the ratio of the products of said first and second means for counting, respectively.

7. The apparatus of claim 6 in which said predetermined forward scattering angular range is between approximately 30 and 60 degrees, said first detector is a totally depleted gold-silicon surface barrier detector approximately 35 microns thick, said second detector is a gold-silicon surface barrier detector at least 100 microns thick, said means for isolating comprising;

an enclosed chamber containing said sample gas, said alpha particle source and said means for detecting; and a plurality of baffles located within said chamber and positioned to allow forward scattering products within said predetermined angular range to impact said means for detecting and to block scattering products not within said predetermined angular range.

8. The apparatus of claim 7 in which said alpha particle source is Polonium 214.

9. A method for developing data useful in determining the ratio of helium to hydrogen in a gaseous sample comprising the steps of:

directing alpha particles into said gaseous sample;

isolating scattering products due to collisions between said alpha particles and said gaseous sample that are within a predetermined forward scattering angular range;

detecting said isolated scattering products; and identifying said detected isolated scattering products due to alpha particle/helium collisions and said isolated scattering products due to alpha particle/hydrogen collisions whereby the ratio of helium to hydrogen can be determined from the products of said identifying step.

10. The method of claim 9 in which said predetermined forward scattering angular range is between approximately 30 and 60 degrees, said identifying step further comprising the steps of:

counting each detected scattering product having a kinetic energy within a predetermined voltage range that impacts a first detector of a detecting means comprising said first detector and a second detector mounted behind and in tandem with said first detector, but does not have sufficient energy to pass through said first detector, thereby identifying an alpha particle/helium collision; and counting each detected scattering product having a kinetic energy sufficiently great to pass through said first detector and be at least partially absorbed by said second detector thereby identifying an alpha particle/hydrogen collision.

* * * * *